(12) United States Patent
Miller, III et al.

(10) Patent No.: US 7,204,799 B2
(45) Date of Patent: Apr. 17, 2007

(54) MICROPHONE OPTIMIZED FOR IMPLANT USE

(75) Inventors: Scott Allan Miller, III, Lafayette, CO (US); Bernd Waldmann, Boulder, CO (US)

(73) Assignee: Otologics, LLC, Boulder, CO (US)

( * ) Notice: Subject to any disclaimer, the term of this patent is extended or adjusted under 35 U.S.C. 154(b) by 254 days.

(21) Appl. No.: 10/982,640

(22) Filed: Nov. 5, 2004

(65) Prior Publication Data

US 2005/0101832 A1    May 12, 2005

Related U.S. Application Data

(60) Provisional application No. 60/518,256, filed on Nov. 7, 2003.

(51) Int. Cl.
*H04R 25/00* (2006.01)

(52) U.S. Cl. .......................................... 600/25; 181/144

(58) Field of Classification Search ................. 600/25; 607/55–57; 381/312, 317–318, 322–324; 181/126–135, 144–151, 157–158, 163–165
See application file for complete search history.

(56) References Cited

U.S. PATENT DOCUMENTS

| | | | |
|---|---|---|---|
| 4,443,666 A | 4/1984 | Cote | 318/113 |
| 4,450,930 A | 5/1984 | Killion | 181/129 |
| 4,504,703 A | 3/1985 | Schneiter et al. | 181/163 |
| 4,532,930 A | 8/1985 | Crosby et al. | 128/419 |
| 4,606,329 A | 8/1986 | Hough | 128/1 |
| 4,607,383 A | 8/1986 | Ingalls | 381/113 |
| 4,621,171 A | 11/1986 | Wada et al. | 381/113 |
| 4,774,933 A | 10/1988 | Hough et al. | 600/25 |
| 4,815,560 A | 3/1989 | Madaffari | 181/129 |
| 4,837,833 A | 6/1989 | Madaffari | 181/129 |
| RE33,170 E | 2/1990 | Byers | 128/419 |
| 4,932,405 A | 6/1990 | Peeters et al. | 128/419 |
| 4,936,305 A | 6/1990 | Ashtiani et al. | 128/420.6 |
| 5,015,224 A | 5/1991 | Maniglia | 600/25 |
| 5,105,811 A | 4/1992 | Kuzma | 128/420.6 |
| 5,163,957 A | 11/1992 | Sade et al. | 623/10 |
| 5,176,620 A | 1/1993 | Gilman | 600/25 |
| 5,277,694 A | 1/1994 | Leysieffer et al. | 600/25 |
| 5,363,452 A | 11/1994 | Anderson | 381/170 |
| 5,411,467 A | 5/1995 | Hortmann et al. | 600/25 |
| 5,456,654 A | 10/1995 | Ball | 600/25 |
| 5,554,096 A | 9/1996 | Ball | 600/25 |
| 5,558,618 A | 9/1996 | Maniglia | 600/25 |
| 5,624,376 A | 4/1997 | Ball et al. | 600/25 |
| 5,702,431 A | 12/1997 | Wang et al. | 607/61 |

(Continued)

*Primary Examiner*—John P. Lacyk
(74) *Attorney, Agent, or Firm*—Marsh Fischmann & Breyfogle, LLP

(57) ABSTRACT

An implantable microphone for use with an implantable hearing instrument that has a reduced vibration sensitivity in comparison with its acoustic sensitivity. The microphone utilizes a plurality of small diaphragms as opposed to a single large diaphragm in order to reduce vibration sensitivity caused by mass loading of the diaphragms by overlying skin and tissue. The acoustic outputs of the plurality of small diaphragms are summed (e.g., acoustically or electronically), which allows the microphone to maintain adequate acoustic sensitivity for hearing augmentation purposes while having a reduced vibration sensitivity. In one aspect, the plurality of diaphragms is formed from a single membrane and a multi-apertured support structure in contact with the membrane. Each aperture in combination with the membrane defines a single diaphragm.

49 Claims, 5 Drawing Sheets

U.S. PATENT DOCUMENTS

| | | | |
|---|---|---|---|
| 5,749,912 A | 5/1998 | Zhang et al. | 607/57 |
| 5,762,583 A | 6/1998 | Adams et al. | 600/25 |
| 5,795,287 A | 8/1998 | Ball et al. | 600/25 |
| 5,800,336 A | 9/1998 | Ball et al. | 600/25 |
| 5,814,095 A | 9/1998 | Muller et al. | 607/57 |
| 5,842,967 A | 12/1998 | Kroll | 600/25 |
| 5,857,958 A | 1/1999 | Ball et al. | 600/25 |
| 5,859,916 A | 1/1999 | Ball et al. | 381/326 |
| 5,881,158 A | 3/1999 | Lesinski et al. | 381/174 |
| 5,888,187 A | 3/1999 | Jaeger et al. | 600/25 |
| 5,897,486 A | 4/1999 | Ball et al. | 600/25 |
| 5,906,635 A | 5/1999 | Maniglia | 607/57 |
| 5,913,815 A | 6/1999 | Ball et al. | 600/25 |
| 5,951,601 A | 9/1999 | Lesinski et al. | 623/10 |

MICROPHONE OPTIMIZED FOR IMPLANT USE

CROSS REFERENCE TO RELATED APPLICATIONS

This application claims priority under 35 U.S.C. 119 to U.S. Provisional Application No. 60/518,256 entitled: "MICROPHONE OPTIMIZED FOR IMPLANT USE," having a filing date of Nov. 7, 2003; the contents of which are incorporated herein as if set forth in full.

FIELD OF THE INVENTION

The present invention relates to implanted microphone assemblies, e.g., as employed in hearing aid instruments, and more particularly, to implanted microphone assemblies having reduced sensitivity to undesired sources of vibration.

BACKGROUND OF THE INVENTION

In the class of hearing aids generally referred to as implantable hearing instruments, some or all of various hearing augmentation componentry is positioned subcutaneously on, within or proximate to a patient's skull, typically at locations proximate the mastoid process. In this regard, implantable hearing instruments may be generally divided into two sub-classes, namely semi-implantable and fully implantable. In a semi-implantable hearing instrument, one or more components such as a microphone, signal processor, and transmitter may be externally located to receive, process, and inductively transmit an audio signal to implanted components such as a transducer. In a fully-implantable hearing instrument, typically all of the components, e.g., the microphone, signal processor, and transducer, are located subcutaneously. In either arrangement, an implantable transducer is utilized to stimulate a component of the patient's auditory system (e.g., tympanic membrane, ossicles and/or cochlea).

By way of example, one type of implantable transducer includes an electromechanical transducer having a magnetic coil that drives a vibratory actuator. The actuator is positioned to interface with and stimulate the ossicular chain of the patient via physical engagement. (See e.g., U.S. Pat. No. 5,702,342). In this regard, one or more bones of the ossicular chain are made to mechanically vibrate causing stimulation of the cochlea through its natural input, the so-called oval window.

For a wearer of an implantable hearing instrument, the sound of a speaker's voice reaches his inner ear by at least three different pathways. One of them goes from the vocal chords through the vocal tract, the outer air, the external ear canal, and the middle ear and to the cochlea; this will be called the air conduction pathway. A second pathway includes the vocal chords, the bony structure of the head and the inner ear; this will be called the bone conduction pathway. In persons without hearing loss, the relative level of acoustic signals reaching the inner ear via these two pathways determines the particular sound quality of an individual's own voice. For persons wearing an implantable hearing instrument, a third pathway is added: sound emanating from the vocal chords passes through the bony structure of the head and reaches the implanted microphone of the implantable middle ear hearing system or fully implantable cochlear implant. The vibration reaches the microphone diaphragm and is amplified just like an external airborne sound would be amplified. Also, in systems employing a middle ear stimulation transducer, the system may produce feedback by picking up and amplifying vibration caused by the stimulation transducer. As such, the bone vibration undesirably limits the maximum achievable gain of the implantable hearing instrument.

As may be appreciated, implantable hearing instruments that utilize an implanted microphone require that the microphone be positioned at a location that facilitates the receipt of acoustic signals. For such purposes, such implantable microphones are most typically positioned in a surgical procedure between a patient's skull and skin, at a location rearward and upward of a patient's ear (e.g., in the mastoid region). Because the diaphragm of an implantable microphone is covered by skin and this skin represents an additional mass loading of the diaphragm, vibration sensitivity of implanted microphones tends to be significantly higher than that of microphones in air. In order to achieve a nearly natural quality of the implant wearer's voice and increase achievable gain, the vibration sensitivity of the implanted microphone has to be reduced compared to its acoustic sensitivity. The aim of the present invention is to design an implantable microphone that achieves these goals.

SUMMARY OF THE INVENTION

A simple dimensional analysis shows that the ratio of vibration sensitivity to sound sensitivity can be reduced by reducing the dimension of the sound receiving element, i.e., the implantable microphone diaphragm. It is generally known that the sensitivity of a microphone diaphragm increases with the area of the diaphragm, e.g., for a circular diaphragm the diameter squared. The vibration sensitivity of the microphone is dominated by the vibrating mass of skin on top of the diaphragm. The effective volume of skin that contributes to the vibration sensitivity may be thought of as dome-shaped as long as the thickness of the layer of skin is above a threshold value. This shape of effective mass can be thought of as similar to the dome shaped mass of effective air over the opening of a Helmholtz cavity. Because the shape of the effective mass remains constant, the vibration sensitivity increases with the volume of the mass and therefore, for a circular diaphragm, increases with the diameter cubed.

It is therefore desirable to design an implantable microphone diaphragm which has the smallest possible area (e.g., diameter for a circular diaphragm) to achieve the lowest ratio of vibration to sound sensitivity and maximize achievable gain. On the other hand, absolute acoustic sensitivity is reduced as the area of the diaphragm becomes smaller, and therefore the input-referred noise floor of the microphone increases. The solution to this dilemma as described in the present invention is to replace one large microphone diaphragm with a plurality of smaller microphone diaphragms, the responsive sum of which will have adequate acoustic sensitivity and adequately low input referred noise while retaining the low ratio of vibration to acoustic sensitivity.

In one aspect of the invention, an implantable microphone is provided that includes a plurality of diaphragms that are operative to transcutaneously receive acoustic signals and output a corresponding plurality of acoustic signals. The microphone further includes at least one electroacoustic transducer operative to receive the plurality of acoustic signals from the plurality of diaphragms and generate an audio output signal in response thereto. That is, an audio output signal may be generated that is indicative of a combination of the plurality of acoustic signals. This audio output signal may subsequently be utilized to drive or actuate an actuator of an implantable hearing instrument and thereby stimulate a component of the implant wearer's auditory system (e.g., tympanic membrane, ossicles and/or cochlea).

Typically, the microphone will include an implantable housing (e.g., made of a biocompatible material) on which the plurality of diaphragms are mounted. These diaphragms may be mounted relative to a chamber within the housing for acoustic transmission purposes. More particularly, the diaphragms may be mounted relative to the chamber such that the chamber is sealed to prevent biological contamination of internal components of the microphone. In this regard, a structure including the plurality of diaphragms or operative to support a plurality of separately formed diaphragms may be sealably positioned across, for example, an aperture leading to the chamber within the housing. In any case, the housing may house the electroacoustic transducer(s) and/or additional hearing instrument componentry.

In one arrangement, where a plurality of diaphragms is mounted relative to a chamber within a housing, the chamber may be designed such that a portion of the chamber is disposed behind each of the plurality of diagrams. In this regard, the acoustic signals generated by each diaphragm may be emitted into the chamber and may be acoustically summed. Accordingly, a single electroacoustic transducer may be operative to provide an audio output signal indicative of the summation of the acoustic signals. That is, a single electroacoustic transducer may be operative to generate an audio output from the acoustically summed signals in the chamber.

The plurality of diaphragms may be separately formed diaphragms that are each mounted relative to a common housing and/or chamber. However, in another arrangement, each of the diaphragms may be at least partially formed from a common membrane structure. For example, the area of the common membrane structure may be sub-divided into a plurality of individual diaphragms, each of which will necessarily have a reduced size relative to the common membrane structure in accordance with the present invention. In order to sub-divide the membrane structure into individual diaphragms, a support structure may be located in contact with at least a portion of the membrane structure. For instance, a grid-like, rigid or semi-rigid, support structure defining a plurality of apertures may be placed in contact with a portion of the membrane structure. In this regard, each of the apertures defined by the support structure, in combination with the membrane, will define each of the diaphragms.

When utilizing a multi-apertured support structure to sub-divide a single membrane into separate diaphragms, it may be necessary to maintain contact between the periphery of each aperture and the membrane throughout an acoustic vibration cycle in order to accurately reproduce received acoustical signals. That is, to accurately reproduce sound the support structure may have to maintain contact between the periphery of each aperture and the membrane structure during both inward and outward diaphragm deflections (i.e., relative to a static position) present during an acoustic vibration cycle. In this regard, the membrane structure may be attached to the periphery of the apertures of the support structure such that each resulting diaphragm maintains contact with the support structure throughout inward and outward diaphragm deflection.

In another arrangement, the support structure may be formed in a structural manner that maintains contact between the peripheries of each aperture and membrane throughout inward and outward deflection of the resulting diaphragms. For instance, a support structure having curved surface with a membrane tensioned over the outside of the curved surface may allow for maintaining contact between the peripheries of each aperture and the membrane through an acoustic vibration cycle. Such a curved support structure may be symmetric about on or more axes. For example, the curved surface may form a half-cylinder or a dome/spherical shape. However, it will be appreciated that such a curved surface may also be irregular. What is important is that the curvature of the surface allows for a diaphragm tensioned over the surface to be tensioned across apertures in the surface in a manner that prevents separation between the surface and the diaphragm during acoustic vibration. Alternatively, a second support structures having identical aperture patterns may be utilized on an opposing side of a membrane structure. In this arrangement two support structures may be disposed on opposing sides of a tensioned membrane.

In another application, a multitude of small diaphragms may be created by pushing an irregular structure against a large membrane. The structure may consist of an open cell foam or a multitude of rigid small balls or differently shaped bodies, sintered or glued together, to define what may be referred to as a frit.

In a further application, an integrated diaphragm/support structure may be utilized. In one arrangement, a block of a single material (e.g., titanium, stainless steel etc.) may be processed to have one or more integrally formed diaphragms. Such processing may include milling, electrochemically milling and/or etching to generate one or more areas of reduced thickness (e.g., diaphragms) within material. In another arrangement, a first material later may be bonded to a different second material layer. Portions of one of the layers may be etched away to define apertures through that layer (i.e., through the support structure). Alternatively, the first and second materials may be selected such that the integrated structure may be heated such that defined diaphragm elements are stretched or tensioned across corresponding apertures of a support structure.

Irrespective of the support structure and/or membrane combination utilized, it will be appreciated that the diaphragms may comprise any suitable biocompatible material. By way of primary example, the diaphragms may comprise a material selected from a group consisting of titanium and titanium-alloys. Likewise, it will be appreciated that in addition to material, the area, thickness, tension, total number, and/or tension of the diaphragms may be selected for acoustic purposes. Finally, it will be noted that different diaphragms may have different properties to facilitate response to different acoustic frequency ranges. For instance, a combination of large and small diaphragms may be utilized that are adapted to respond to low and high frequencies, respectively.

In another application, the microphone may further include an electrical summation means for combining audio outputs from at least two electro-acoustical transducers. In this regard, the summation of the acoustic signals from individual diaphragms may be effected electrically (i.e., by combinatively processing the output of the electroacoustic transducers) or as a combination of acoustical summation (i.e., where each single electroacoustic transducer may provide an output responsive to a small group of diaphragms) and electrical summation (i.e., by combinatively processing the output of the electroacoustic transducers). Accordingly, the audio output signal generated by each of these electroacoustic transducers may be combined to generate a composite output signal, the responsive sum of which will have adequate acoustic sensitivity for hearing purposes. In a similar manner, output signals from a plurality of separate microphones may be combined into a single composite audio output signal.

In one application, a multitude of electroacoustic transducers may be utilized wherein each electroacoustic transducer is placed close to each or a group of the plurality of diaphragms. Such individual electroacoustic transducers may be realized either using conventional manufacturing methods or by using microelectromechanical systems (MEMS) technology. In one embodiment, a plurality of electroacoustic transducers corresponding to the plurality of diaphragms may be utilized. In this regard, each electroacoustic transducer may be juxtaposed adjacent to a corresponding diaphragm, which may increase the overall sensitivity of the microphone.

According to another aspect of the present invention, a method for use in an implantable hearing instrument is provided that allows for achieving a low ratio of vibration to sound sensitivity while enhancing achievable gain. The method includes receiving at least first and second acoustic signals from at least first and second implanted microphone diaphragms and summing outputs associated with the acoustic signals to generate a composite output signal. This composite output signal may then be utilized to generate a stimulation signal for stimulating an auditory component of a patient. As will be appreciated, the present aspect allows for combining the acoustic signals from a plurality of microphone diaphragms such that vibration sensitivity may be reduced while maintaining adequate acoustic sensitivity for hearing purposes.

In a first arrangement, the signals form the diaphragms may be acoustically summed. In this regard, two or more acoustic output signals form the diaphragms may be output into a common chamber to generate an acoustically summed signal. This acoustically summed signal may then be received by an electroacoustic transducer that is operative to generate the composite output signal. In another arrangement, outputs for the diaphragms (e.g., acoustic output signals) are received at two or more electroacoustic transducers. These transducers in turn generate a corresponding number of electrical outputs that are indicative of the received acoustic signals. These electrical outputs may then be summed to generate the composite output signal.

According to another aspect of the present invention, an implantable hearing instrument is provided that includes a microphone having a plurality of diaphragms operative to transcutaneously receive acoustic signals and output a corresponding plurality of acoustic signals. The microphone further includes at least one electro-acoustic transducer to receive the plurality of acoustic signals and generate an audio output signal in response thereto. The hearing instrument further includes an actuator operative to receive the audio output signal and stimulate a component of an implant wearer's auditory system in accordance with the audio output signal in order to generate a sensation of sound.

The actuator may be any one of a plurality of different types of actuators. For instance, in a middle ear hearing instrument, an actuator may be operative to mechanically stimulate (e.g., vibrate) one or more of the ossicles, which in turn causes stimulation of the cochlea through it's natural input, the oval window. Such mechanical stimulation may be through direct coupling with the ossicular chain or via a magnetic connection. Alternatively, the actuator may generate an audio signal for use in stimulating the tympanic membrane which in turn stimulates the ossicular chain and thereby the cochlea. Alternatively, the actuator may be operative to directly stimulate the cochlea and thereby produce the sensation of sound.

DETAILED DESCRIPTION OF THE INVENTION

Reference will now be made to the accompanying drawings, which at least assist in illustrating the various pertinent features of the present invention. In this regard, the following description of a hearing aid device is presented for purposes of illustration and description. Furthermore, the description is not intended to limit the invention to the form disclosed herein. Consequently, variations and modifications commensurate with the following teachings, and skill and knowledge of the relevant art, are within the scope of the present invention. The embodiments described herein are further intended to explain the best modes known of practicing the invention and to enable others skilled in the art to utilize the invention in such, or other embodiments and with various modifications required by the particular application(s) or use(s) of the present invention.

Figure 1:
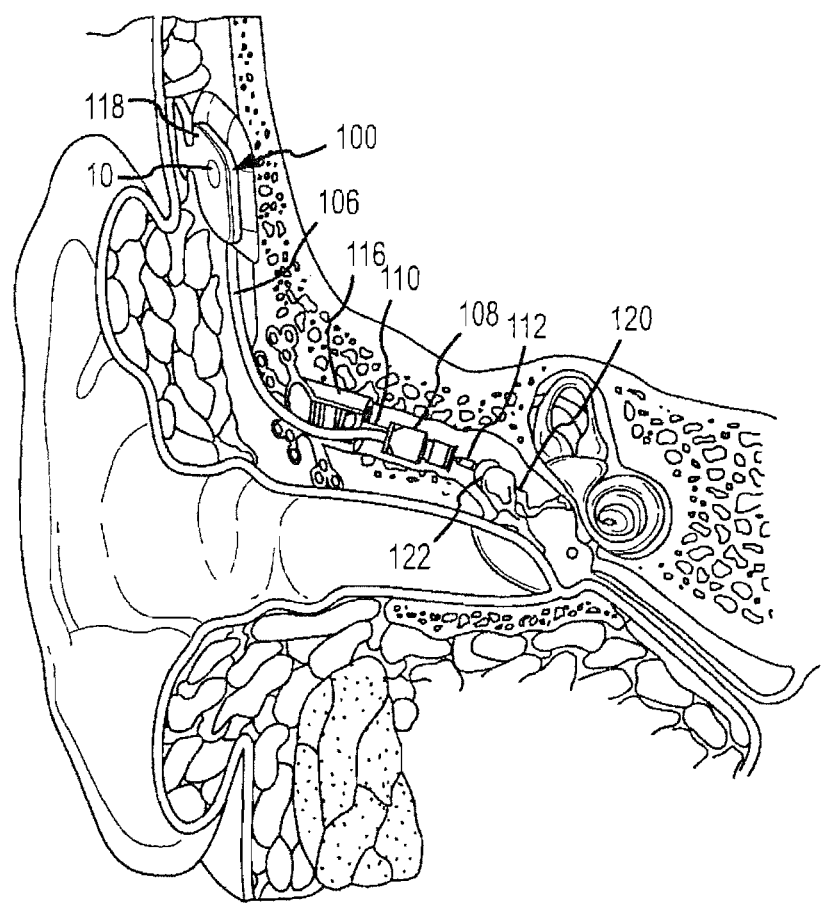
FIG. 1 illustrates a fully implantable hearing instrument.

Hearing Instrument System:

FIG. 1 illustrates one application of the present invention. As illustrated, the application comprises a fully implantable hearing instrument system. As will be appreciated, certain aspects of the present invention may be employed in conjunction with semi-implantable hearing instruments as well as fully implantable hearing instruments, and therefore the illustrated application is for purposes of illustration and not limitation.

In the illustrated system, a biocompatible implant housing 100 is located subcutaneously on a patient's skull. The implant housing 100 includes a signal receiver 118 (e.g., comprising a coil element) and an integrated microphone assembly having a diaphragm 10 that is positioned to receive acoustic signals through overlying tissue. The implant housing 100 may be utilized to house a number of components of the fully implantable hearing instrument. For instance, the implant housing 100 may house an energy storage device, a microphone transducer, and a signal processor. Various additional processing logic and/or circuitry components may also be included in the implant housing 100 as a matter of design choice. Typically, the signal processor within the implant housing 100 is electrically interconnected via wire 106 to a transducer 108.

The transducer 108 is supportably connected to a positioning system 110, which in turn, is connected to a bone anchor 116 mounted within the patient's mastoid process (e.g., via a hole drilled through the skull). The transducer 108 includes a connection apparatus 112 for connecting the transducer 108 to the ossicles 120 of the patient. In a connected state, the connection apparatus 112 provides a communication path for acoustic stimulation of the ossicles 120, e.g., through transmission of vibrations to the incus 122.

During normal operation, acoustic signals are received subcutaneously at the diaphragm 10. Upon receipt of the acoustic signals, a signal processor within the implant housing 100 processes the signals to provide a processed audio drive signal via wire 106 to the transducer 108. As will be appreciated, the signal processor may utilize digital processing techniques to provide frequency shaping, amplification, compression, and other signal conditioning, including conditioning based on patient-specific fitting parameters. The audio drive signal causes the transducer 108 to transmit vibrations at acoustic frequencies to the connection apparatus 112 to effect the desired sound sensation via mechanical stimulation of the incus 122 of the patient.

To power the fully implantable hearing instrument system of FIG. 1, an external charger (not shown) may be utilized to transcutaneously re-charge an energy storage device within the implant housing 100. In this regard, the external charger may be configured for disposition behind the ear of the implant wearer in alignment with the implant housing 100. The external charger and the implant housing 100 may each include one or more magnets to facilitate retentive juxtaposed positioning. Such an external charger may include a power source and a transmitter that is operative to transcutaneously transmit, for example, RF signals to the signal receiver 118. In this regard, the signal receiver 118 may also include, for example, rectifying circuitry to convert a received signal into an electrical signal for use in charging the energy storage device. In addition to being operative to recharge the on-board energy storage device, such an external charger may also provide program instructions to the processor of the fully implantable hearing instrument system.

Microphone:

As noted above, it is desirable to design an implantable microphone diaphragm having the smallest possible area (e.g., diameter for a circular diaphragm) to achieve the lowest ratio of vibration to sound sensitivity and thereby maximize achievable gain. However, absolute acoustic sensitivity is reduced as the area of the diaphragm becomes smaller, and therefore the input referred noise floor of the microphone increases. To strike a balance between these competing goals, the present invention utilizes a multitude of smaller microphone diaphragms, the responsive sum of which will have adequate acoustic sensitivity and adequately low input referred noise while retaining the low ratio of vibration to acoustic sensitivity.

In a first embodiment, a plurality of individual diaphragm elements are disposed relative to a common chamber that allows for acoustically summing the output of the individual diaphragm elements. In one arrangement of the acoustic summing embodiment shown in FIGS. 2A–2D, a large primary diaphragm 10 of the microphone assembly is subdivided into multiple smaller diaphragm elements 12 by placing a grid-like, rigid or semi-rigid, support structure 20 having a plurality of apertures 26 in contact relation with the diaphragm 10.

Figure 2A:
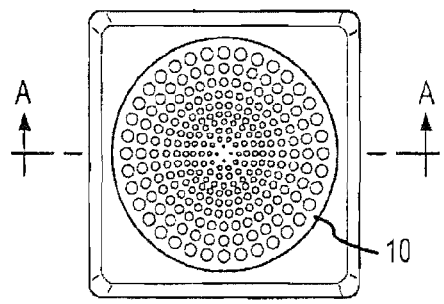
FIGS. 2A and 2B show plan and cross-sectional views, respectively, of a first acoustic summation embodiment of the present invention.
Figure 2B:
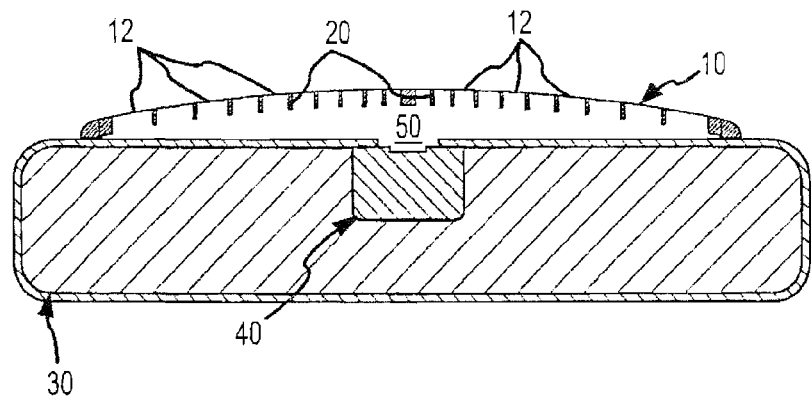
Figure 2C:
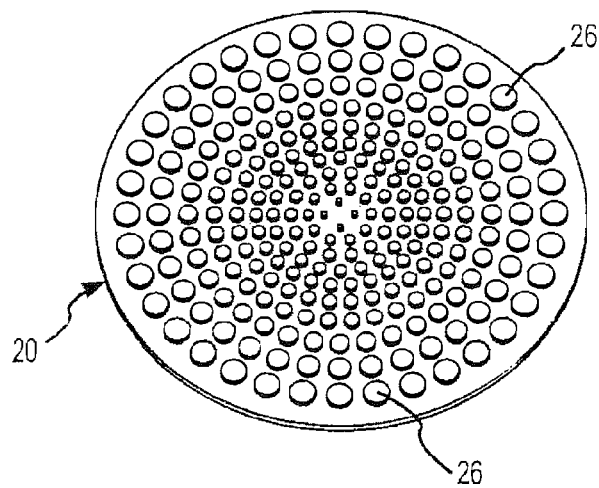
FIG. 2C is a perspective view of a grid-like structure used in the embodiment of FIGS. 2A and 2B.
Figure 2D:
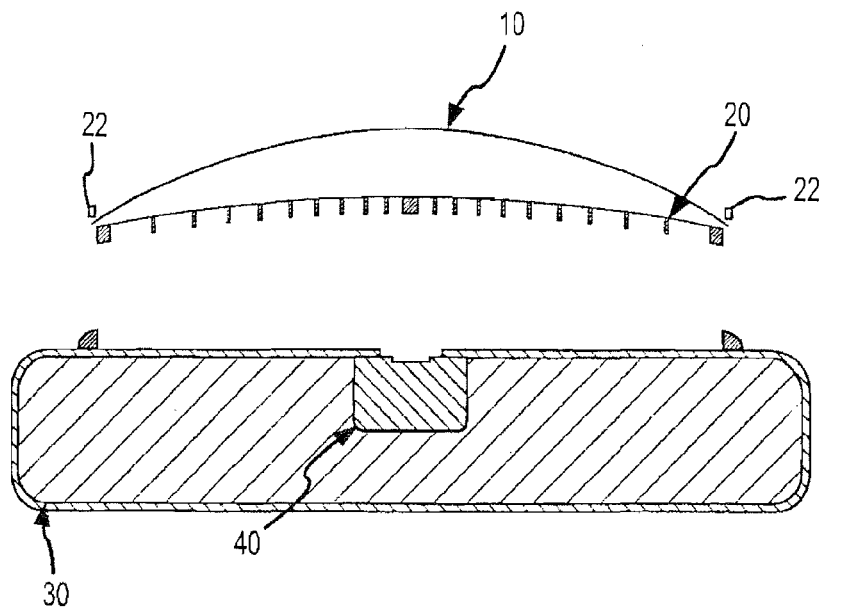
FIG. 2D is an exploded cross-sectional view of the embodiment of FIG. 2A.

As shown in FIG. 2D, the diaphragm 10, which is formed from a single membrane, may be tensioned over the curved outside surface of the support structure 20. Once tensioned over the support structure 20, a retaining ring 22 may clamp the diaphragm 10 and support structure to the housing 30. The diaphragm 10 may be tensioned across each aperture 26 such that the resulting diaphragm elements 12 are operative to vibrate in response to received acoustic signals (e.g., sound). By disposing the diaphragm 10 on the outside curvature of the support structure 20, contact may be maintained between the peripheries of the apertures 26 and the diaphragm 10 throughout an acoustic vibration cycle of the resulting diaphragm element 12. Further, an adhesive may be applied to the peripheries of the apertures 26 to adhere the diaphragm 10 to the support structure 20. Though shown as utilizing a generally dome-shaped support structure 20, it will be appreciated that any curved support structure including a plurality of apertures may be utilized to create a multi-diaphragm microphone having a single membrane tensioned over its outside curved surface.

For enhanced ruggedness and/or acoustic matching, a thin layer of a selected, bio-compatible material (e.g., a silicone-containing material) may be provided (e.g., cast) over the diaphragm 10, or over an external support structure 20 if utilized.

The diaphragm 10 and support structure 20 may be supportably interconnected to the implant housing 100 as shown in FIG. 1, or, supportably interconnected to a separate implantable microphone housing that may be, for example, electrically interconnected to the implant housing 100. Though discussed herein as being interconnected to a separate microphone housing 30 as shown in FIGS. 2A–2D, it will be appreciated that various aspects of the invention are equally applicable to an embodiment interconnected to an implant housing 100.

A microphone transducer 40 may be disposed within the microphone housing 30 that is operable to provide an output signal, for example via wire 42, that responsive to movement of the multiple diaphragm elements 12. As may be appreciated, the output signal from the microphone transducer 40 may be amplified/processed/conditioned and supplied to a middle ear transducer or cochlear implant for stimulation thereof. An example of a middle ear stimulation transducer arrangement is described in U.S. Pat. No. 6,491,622, hereby incorporated by reference.

Of note, sound pressure variations on the outside of diaphragm 10 will cause movement of the plurality of the small diaphragm elements 12. The movements of diaphragm elements 12 will combinatively result in pressure variations in a trapped volume of air in one or a plurality of interconnected chambers 50 behind the diaphragm elements 12. In turn, such pressure variations will be reflected by the output signal from the microphone transducer 40. In this way a summation of the output of the individual diaphragm elements 12 is effected acoustically.

The microphone transducer 40 may be defined by any of a wide variety of electroacoustic transducers, including for example, capacitor arrangements (e.g., electret microphones) and electrodynamic arrangements. Further, one or a plurality of tuning elements may be employed in conjunction with the microphone transducer 40 to optimize frequency response. For example, one or more additional diaphragms may be located in chamber(s) 50.

Figure 3:
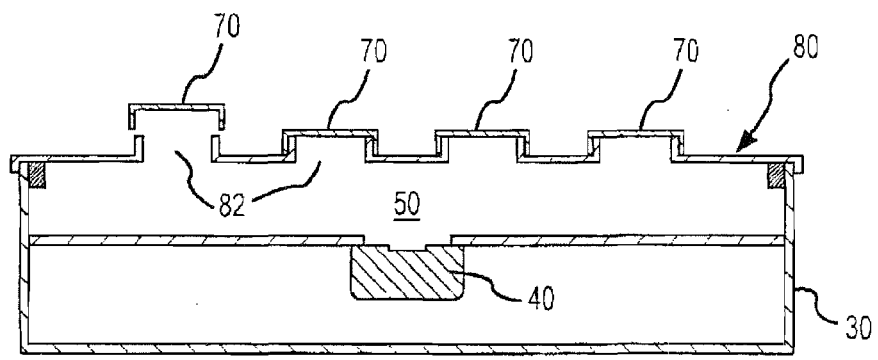
FIG. 3 shows a cross-sectional view of a second acoustic summation embodiment of the present invention.

In another acoustic summing embodiment shown in FIG. 3 a plurality of individual diaphragm elements 70 are attached to a support structure 80. That is, as opposed to utilizing a single membrane tensioned over the outside surface of a curved support structure, this arrangement utilizes a plurality of individually formed diaphragm elements 70. In this arrangement, the individual diaphragm elements 70 are attached (e.g., adhered) to the support structure 80 and extend across corresponding apertures 82 within the support structure 80. Such diaphragm elements 70 may be pre-tensioned, or, may be tensioned once interconnected to the support structure 80. In the latter regard, the diaphragm elements 70 may be, for example, heat treated to produce a desired tension.

Figure 4A:
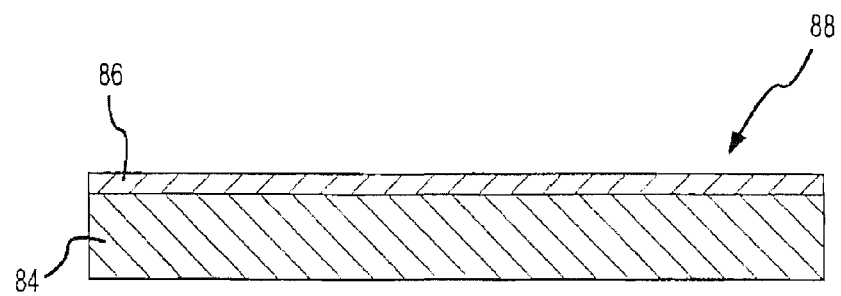
FIGS. 4A and 4B show a cross-sectional view of a support structure including a plurality of integrally formed diaphragms.
Figure 4B:
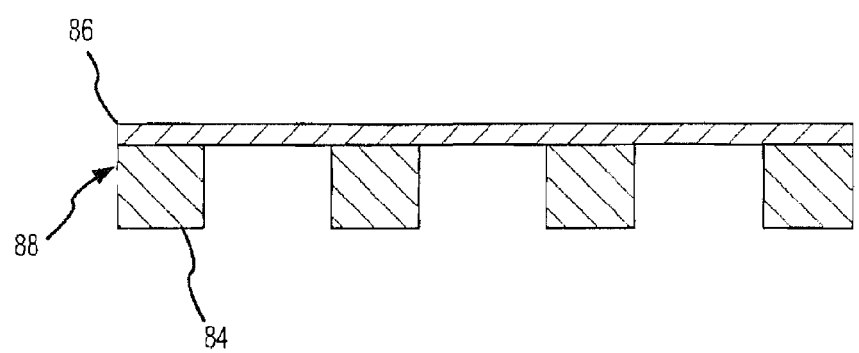

The support structure 80 is sized to be supportably interconnected to the microphone housing 30. Likewise, the plurality of individual diaphragm elements 70 may be disposed relative to a common chamber 50 for acoustic summation. Generally, the support structure 80 and the individual diaphragm elements 70 will hermetically seal the housing 30 prevent contamination by body fluids. In further arrangement that may be utilized with the embodiment shown in FIG. 3 an integrated diaphragm/support structure is provided as shown in FIGS. 4A and 4B. That is, as opposed to utilizing separately formed diaphragm elements 70 attached to a support structure 80, a single structure including a plurality of integrally defined diaphragms is utilized. In such approach, a first material layer 84 may be bonded to a different second material layer 86 that will define a diaphragm in the resulting integrated support structure 88. Then, portions of the first material layer 84 may be etched away to define areas of reduced thickness in the support structure 88. Optionally, the first and second materials may be selected so that the integrated support structure 88 may be heated to an annealing temperature that yields a plurality of diaphragm elements that are stretched, or tensioned, across corresponding apertures of the integrated support structure 88. Further, it will be appreciated that diaphragms defined by areas of reduced thickness may be machined into a single material (e.g., titanium) to form an integral one-piece structure.

Figure 5:
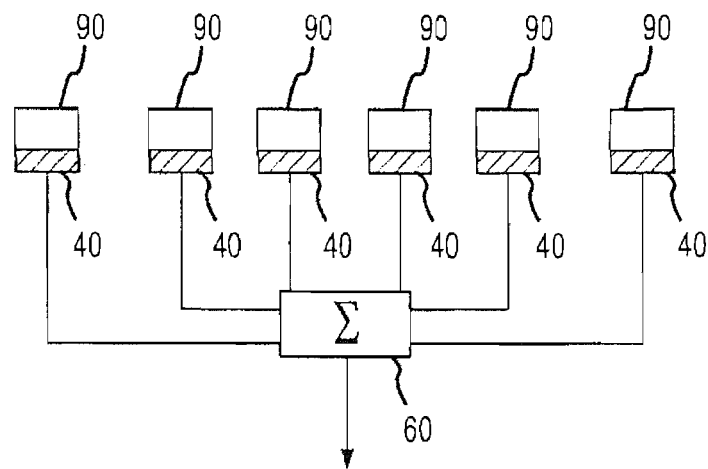
FIG. 5 shows a schematic of an electrical summation embodiment of the present invention.

In a second embodiment of the present invention, the output signals of a plurality of small diaphragm elements are electronically summed. As shown in FIG. 5 plurality of individual diaphragm elements 90 are juxtaposed relative to a corresponding plurality of microphone transducers 40. The output of each microphone transducer 40 is electronically summed by a summation circuit 60. That is, the summation circuit 60 combines the outputs from the transducers 40. Accordingly, the output signals generated by each of these transducers 40 may be combined to generate a composite output signal, the responsive sum of which will have an adequate acoustic sensitivity for hearing purposes.

The plurality of individual diaphragm elements 90 and corresponding transducers may be individual units (e.g., separate microphones) or may share one or more structures. For instance, the plurality of diaphragm elements may be formed into an integrated structure as discussed above, or share a common diaphragm.

Figure 6:
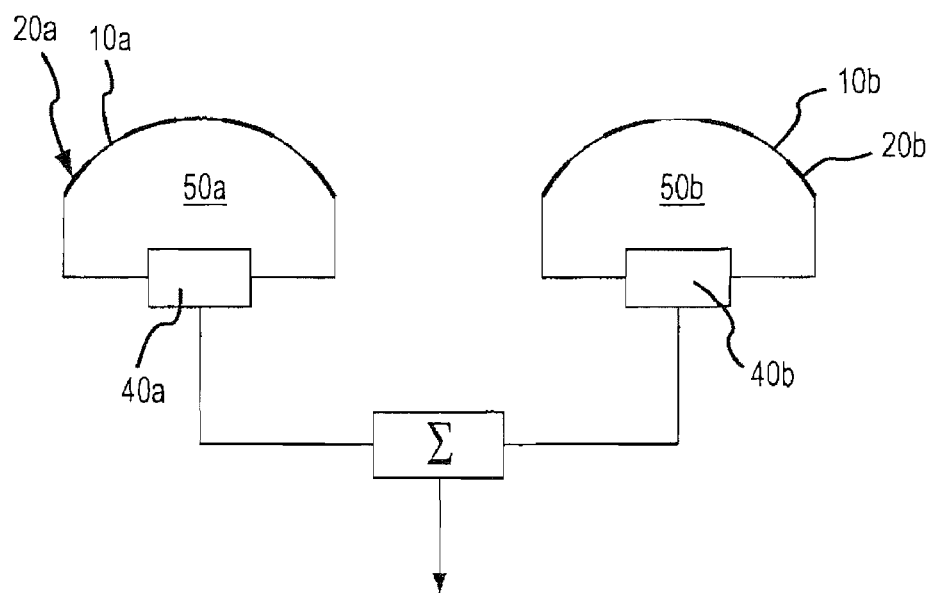
FIG. 6 shows a schematic of a combined acoustic and electrical summation embodiment of the present invention.

FIG. 6 shows a combined embodiment that utilizes both acoustic and electrical summation. As shown, the embodiment utilizes first and second support structures 20a, 20b each having a plurality of apertures that in combination with tensioned diaphragms 10a, 10b define a plurality of diaphragm elements. Each set of diaphragm elements are disposed relative to an acoustic summation chamber 50a, 50b, respectively. As discussed above, the output signals of the diaphragms elements are acoustically summed in the chambers 50a, 50b. The transducers 40a and 40b are then able to generate first and second outputs indicative of the acoustically summed output signals. The first and second outputs may then be electrically summed by summation circuit 60.

Those skilled in the art will appreciate variations of the above-described embodiments that fall within the scope of the invention. As a result, the invention is not limited to the specific examples and illustrations discussed above, but only by the following claims and their equivalents.

The invention claimed is:

1. A implantable microphone, comprising:
   a plurality of diaphragms operative to transcutaneously receive acoustic signals and output of a corresponding plurality of acoustic signals; and
   at least one electroacoustic transducer operative to receive said plurality of acoustic signals and generate an audio output signal in response thereto, said audio output signal being operative to actuate an actuator of a hearing instrument.

2. The microphone of claim 1, further comprising
   a housing having an internal chamber with an aperture thereto.

3. The microphone of claim 2, wherein a portion of said chamber is disposed behind each said diaphragm.

4. The microphone of claim 1, wherein each of said plurality of diaphragms shares a common membrane structure.

5. The microphone of claim 4, further comprising:
   a support structure in face-to-face contact with at least a portion of said membrane structure.

6. The microphone of claim 5, wherein said support structure includes a corresponding plurality of apertures, wherein each said aperture in combination with said membrane, define each said diaphragm.

7. The microphone of claim 6, wherein said membrane is tensioned across said apertures.

8. The microphone of claim 6, wherein a periphery of each said aperture maintains contact with said membrane while said diaphragm deflects inward and outward.

9. The microphone of claim 8, wherein said membrane is bonded to said periphery of each said aperture.

10. The microphone of claim 8, wherein at least a portion of said support structure is curved and said membrane is tensioned over an outside surface said curved portion.

11. The microphone of claim 1, further comprising:
    an electrical summation means for combining audio output signals from at least two electroacoustic transducers to generate a composite audio output signal.

12. The microphone of claim 11, further comprising:
    a corresponding plurality of electroacoustic transducers.

13. The microphone of claim 12, wherein each one of said plurality of electroacoustic transducers is juxtaposed relative to a corresponding one of said plurality of diaphragms.

14. An implantable microphone, comprising:
    a housing having an internal chamber with an aperture thereto;
    a structure sealably positioned across said aperture, wherein said structure further includes a plurality of diaphragms operative to transcutaeously receive acoustic signals and output a corresponding plurality of acoustic signals into said chamber;
    an electroacoustic transducer operatively interconnected to said chamber for receiving said plurality of acoustic signals and generating an audio output signal, said audio output signal being operative to actuate an actuator of a hearing instrument.

15. The microphone of claim 14, wherein said structure and said diaphragms are an integrally formed unit.

16. The microphone of claim 15, wherein said diaphragms comprise areas having a reduced thickness within said structure.

17. The microphone of claim 14, wherein said structure further comprises:
a membrane layer; and
a support layer in face-to-face contact with at least a portion of said membrane layer.

18. The microphone of claim 17, wherein said support layer includes a corresponding plurality of apertures, wherein each said aperture in combination with said membrane, define each said diaphragm.

19. The microphone of claim 18, wherein said membrane is tensioned across said apertures.

20. The microphone of claim 18, wherein said support layer maintains contact with the membrane about the peripheries of said apertures.

21. The microphone of claim 18, wherein at least a portion of said support layer is curved and said membrane is tensioned over an outside surface said curved portion.

22. The microphone of claim 14, wherein said plurality of diaphragms have a uniform size.

23. The microphone of claim 14, wherein said plurality of diaphragms include at least a first diaphragm adapted to facilitate response to a first acoustic frequency range and at least a second diaphragm adapted to facilitate response to a second acoustic frequency range, wherein said first and second acoustic frequency ranges are different.

24. The microphone of claim 14, wherein said housing, said structure and said diaphragms comprise a biocompatible material.

25. The microphone of claim 24, wherein said biocompatible material includes titanium.

26. An implantable microphone comprising:
a structure having a curved portion with at least two apertures extending through said curved portion;
a membrane disposed over an outside surface of said curved portion of said structure, wherein each said aperture and said membrane collectively define a diaphragm;
at least one electroacoustic transducer operative to receive acoustic signals from at least one said diaphragm and generate an audio output signal in response thereto.

27. The microphone of claim 26, wherein said membrane is tensioned over said curved portion of said structure.

28. The microphone of claim 26, wherein said membrane is affixed about a perimeter of each said aperture.

29. The microphone of claim 26, wherein said structure is sealably positioned across an aperture in an implantable housing.

30. The microphone of claim 29, wherein said electroacoustic transducer is positioned within said housing.

31. The microphone of claim 29, wherein said housing further comprises:
an internal chamber.

32. The microphone of claim 31, wherein said internal chamber is adapted to receive said acoustic signals from each said diaphragm.

33. The microphone of claim 26, further comprising:
at least a second electroacoustic transducer operative to receive acoustic signals from at least one said diaphragm and generate an audio output signal in response thereto; and
an electrical summation means for combining audio output signals from at least two electroacoustic transducers to generate a composite audio output signal.

34. The microphone of claim 26, wherein said structure is curved over a majority of its surface.

35. The microphone of claim 34, wherein said structure is substantially dome-shaped.

36. A method for use in an implantable hearing instrument, comprising the steps of:
receiving first and second acoustic signals from first and second implanted microphone diaphragms, respectively;
summing outputs associated with said first and second diaphragms that are indicative of said first and second acoustic signals, respectively, to generate a composite output signal; and
using said composite output signal, generating a stimulation signal for stimulating an auditory component of a patient.

37. The method of claim 36, wherein said receiving step comprises:
transcutaneously receiving an acoustic sound at said first and second implanted microphone diaphragms; and
outputting first and second acoustic outputs in response to said acoustic sound.

38. The method of claim 37, wherein said outputting step comprises:
outputting said first and second acoustic outputs into a common chamber.

39. The method of claim 38, wherein said summing step is performed acoustically to generate an acoustically summed signal.

40. The method of claim 39, wherein an electroacoustic transducer receives said acoustically summed signal and generates said composite output signal.

41. The method of claim 36, wherein said receiving step comprises:
receiving at least one output associated with at least one of said first and second diaphragms at a first electroacoustic transducer; and
receiving at least one output associated with at least one of said first and second diaphragms at a second electroacoustic transducer.

42. The method of claim 41, wherein said first and second electroacoustic transducers generate first and second electrical outputs.

43. The method of claim 41, wherein said summing step comprises electrically summing said first and second electrical outputs to generate said composite output signal.

44. An implantable hearing instrument, comprising:
a microphone, including:
a plurality of diaphragms operative to transcutaneously receive acoustic signals and output of a corresponding plurality of acoustic signals; and
at least one electro-acoustic transducer operative to receive said plurality of acoustic signals and generate an audio output signal in response thereto;
an actuator operative to receive said audio output signal and generate a stimulation signal for stimulating an auditory component of a patient.

45. The instrument of claim 44, wherein said actuator comprises a vibratory actuator operative to mechanically vibrate in accordance with said audio output signal.

46. The instrument of claim 45, wherein said vibratory actuator vibrates an ossicle of the patient via physical engagement.

47. The instrument of claim 44, wherein said actuator comprises an acoustic actuator operative to generate an acoustic output in accordance with said audio output signal.

48. The instrument of claim 47, wherein said acoustic actuator acoustically stimulates a tympanic membrane of the patient.

49. The instrument of claim 44, wherein said actuator comprises a cochlear actuator operative to generate electrical stimulation signals in response to said audio output signal.

* * * * *

UNITED STATES PATENT AND TRADEMARK OFFICE
CERTIFICATE OF CORRECTION

PATENT NO. : 7,204,799 B2
APPLICATION NO. : 10/982640
DATED : April 17, 2007
INVENTOR(S) : Miller et al.

It is certified that error appears in the above-identified patent and that said Letters Patent is hereby corrected as shown below:

Column 10
Line 62, delete "transcutaeously-" and insert therefore --transcutaneously--.

Signed and Sealed this

Third Day of July, 2007

JON W. DUDAS
*Director of the United States Patent and Trademark Office*